United States Patent [19]

Leighton

[11] 4,277,017
[45] Jul. 7, 1981

[54] GEAR DRIVE FOR SEAL-LESS COUNTER CURRENT CHROMATOGRAPHY

[75] Inventor: Stephen B. Leighton, Silver Spring, Md.

[73] Assignee: The United States of America as represented by the Department of Health, Education and Welfare, Washington, D.C.

[21] Appl. No.: 83,829

[22] Filed: Oct. 11, 1979

[51] Int. Cl.³ .................... B04B 9/00; B04B 11/00
[52] U.S. Cl. .................................. 233/25; 210/325; 233/16
[58] Field of Search .............. 233/16, 17, 23 R, 23 A, 233/24, 25, 1 R, 1 D, 1 A; 210/325, 657, 198 C; 74/797, 793, 750 R

[56] References Cited

U.S. PATENT DOCUMENTS

| | | | |
|---|---|---|---|
| 3,420,436 | 1/1969 | Ito | 233/17 |
| 3,775,309 | 11/1973 | Ito | 210/657 |
| 3,856,669 | 12/1974 | Ito | 210/635 |
| 3,986,442 | 10/1976 | Khoja | 233/14 R |
| 3,994,805 | 11/1976 | Ito | 210/635 |
| 4,051,025 | 9/1977 | Ito | 233/1 A |
| 4,058,460 | 11/1977 | Ito | 233/25 |
| 4,162,761 | 7/1979 | Ito | 233/24 |
| 4,228,950 | 10/1980 | Ito | 233/25 |

*Primary Examiner*—Robert W. Jenkins
*Attorney, Agent, or Firm*—Browdy and Neimark

[57] ABSTRACT

A flow-through coil planet centrifuge mechanism with variable rotation-revolution (r/R) speed ratios, which does not employ rotating seals. The rotation and revolution rates are continuously adjustable by using separate variable-speed drive motors. A system of gearing and belts compensates for the rotation and revolution of the centrifuge column relative to a stationary supporting frame structure to avoid twisting of the flow tubes. A first motor drives a pair of spider assemblies arranged coaxially with a column-supporting spool. One spider assembly has planetary gearing cooperating with a fixed gear belt to rotate the column relative to the spool. The other spider assembly has planetary gearing driven by a second motor and coupled to the column support spool so that the spool revolves relative to the stationary frame structure and simultaneously the column rotates relative to the spool.

12 Claims, 5 Drawing Figures

GEAR DRIVE FOR SEAL-LESS COUNTER CURRENT CHROMATOGRAPHY

FIELD OF THE INVENTION

This invention relates to centrifugal liquid processing apparatus, and more particularly to a coil centrifuge apparatus of the flow-through type having a variable rotation/revolution ratio and not employing rotating seals.

BACKGROUND OF THE INVENTION

Coil planet centrifuge devices for particle separation were first developed employing end-closed coiled tubes. This type of centrifuge device is described in U.S. Pat. No. 3,420,436 to Y. Ito. This original type of centrifuge apparatus was designed to obtain predetermined specific rotation/revolution (r/R) ratios of the column holder, such as 1/100, 1/200, 1/300 and 1/500. The capability of the system has been demonstrated by the separation of particles using both single phase and two-phase solvent systems.

However, the above-mentioned prior system lacks continuous flow-through capability, resulting in limited efficiency and in difficulty in the continuous monitoring and fractionization of the separated samples.

Recently, various types of flow-through centrifuge devices have been developed to carry out countercurrent chromatography and cell separations without the use of rotating seals. However, all these systems have fixed r/R values, of either 1 or zero, and also lack versatility in separation.

The following prior patents illustrate prior systems as above described, and include additional known prior art: the patents to Ito and Ito et al. U.S. Pat. Nos. 3,420,436; 3,775,309; 3,856,669; 3,994,805; 4,051,025; and 4,058,460; and the Khoja et al. U.S. Pat. No. 3,986,442. Also known are applications Ser. No. 856,172; Ser. No. 966,329; and Ser. No. 969,570 of Dr. Ito.

SUMMARY OF THE INVENTION

Accordingly, a main object of the invention is to overcome the deficiencies and disadvantages of the above-mentioned prior art centrifuge devices.

A further object of the invention is to provide an improved coil planet centrifuge device which has continuous flow-through capability, which is highly efficient, which facilitates the continuous monitoring and fractionation of separated samples, and which does not employ rotating seals.

A still further object of the invention is to provide an improved coil planet centrifuge apparatus of the flow-through type which does not employ rotating seals, which provides continuous adjustability of the rotation/revolution (r/R) ratio of its column holder and which therefore is continuously adjustable to meet a wide range of separation requirements, and which has a high degree of versatility in separation.

A still further object of the invention is to provide an improved coil planet centrifuge apparatus of the flow-through type which includes separate continuously variable-speed motors respectively for rotating its column holder around its central axis and for simultaneously revolving the column holder around the main central axis of the apparatus, whereby to provide continuous adjustability of the rotation/revolution (r/R) ratio of the column holder and to enable the apparatus to cover a wide range of separation requirements with high efficiency and versatility.

A still further object of the invention is to provide an improved coil planet centrifuge apparatus of the flow-through type with continuous adjustability of the rotation/revolution ratio (r/R) of its column holder over a wide range of separation requirements and having improved means of avoiding twisting of its flow tubes without requiring the use of rotating seals.

A still further object of this invention is to provide an improved coil planet centrifuge apparatus of the flow-through type with variable rotation/revolution speed ratios, which does not employ rotating seals, wherein the flow tubes are rotated synchronously with the column in a direction to avoid twisting by the use of an improved system of gearing and belts which compensates for the rotation and revolution of the centrifuge column relative to the stationary supporting frame structure of the apparatus and which is provided with a pair of driven spider assemblies arranged coaxially with a column-supporting spool member, and wherein a first adjustable-speed motor drives the spider assemblies, one of the spider assemblies having planetary gearing cooperating with a fixed gear belt to rotate the column relative to the spool member and the other spider assembly having planetary gearing driven by a second adjustable-speed motor and coupled to the column-supporting spool member so that the spool member revolves relative to the stationary supporting frame structure while simultaneously the column rotates on the spool member.

BRIEF DESCRIPTION OF THE DRAWINGS

Further objects and advantages of the invention will become apparent from the following description and claims, and from the accompanying drawings, wherein:

DESCRIPTION OF A PREFERRED EMBODIMENT

Figure 1:
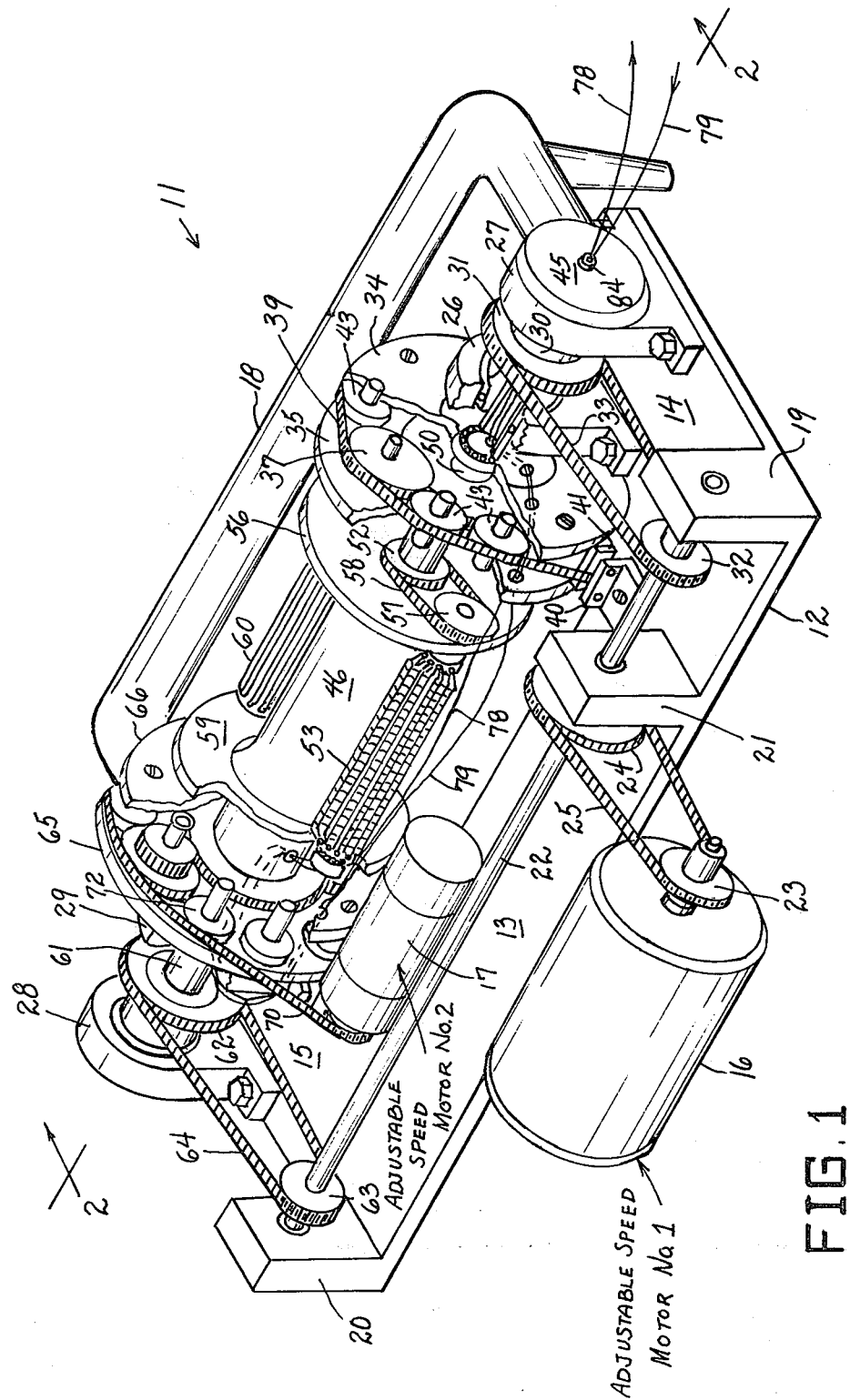
FIG. 1 is a perspective view, with parts broken away, of a coil planet centrifuge apparatus constructed in accordance with the present invention.

Referring to the drawings, 11 generally designates a centrifugal liquid processing apparatus constructed in accordance with the present invention. The apparatus 11 comprises a supporting frame including a generally U-shaped base plate 12 having a main longitudinal portion 13 and respective transverse end arm portions 14 and 15. Rigidly secured longitudinally to the front edge of portion 13 is a first adjustable-speed motor 16. Also rigidly secured longitudinally to the rear margin of portion 13 is a second adjustable-speed motor 17.

An elongated U-shaped hollow tubular frame arm 18 is rigidly secured to the rear edges of the transverse base plate arms 14 and 15.

Vertical upstanding corner lugs 19 and 20 are integrally formed on the front corners of base plate 12, and a similar vertical upstanding lug 21 is integrally formed on the front margin of said base plate in longitudinal alignment with upstanding lugs 19 and 20 adjacent to but spaced from lug 19. A longitudinally extending shaft 22 is journalled in the lugs 19, 20 and 21. Motor 16 is provided with a drive gear 23 which is drivingly coupled to a gear 24 on shaft 21 via a toothed belt 25.

Figure 2:
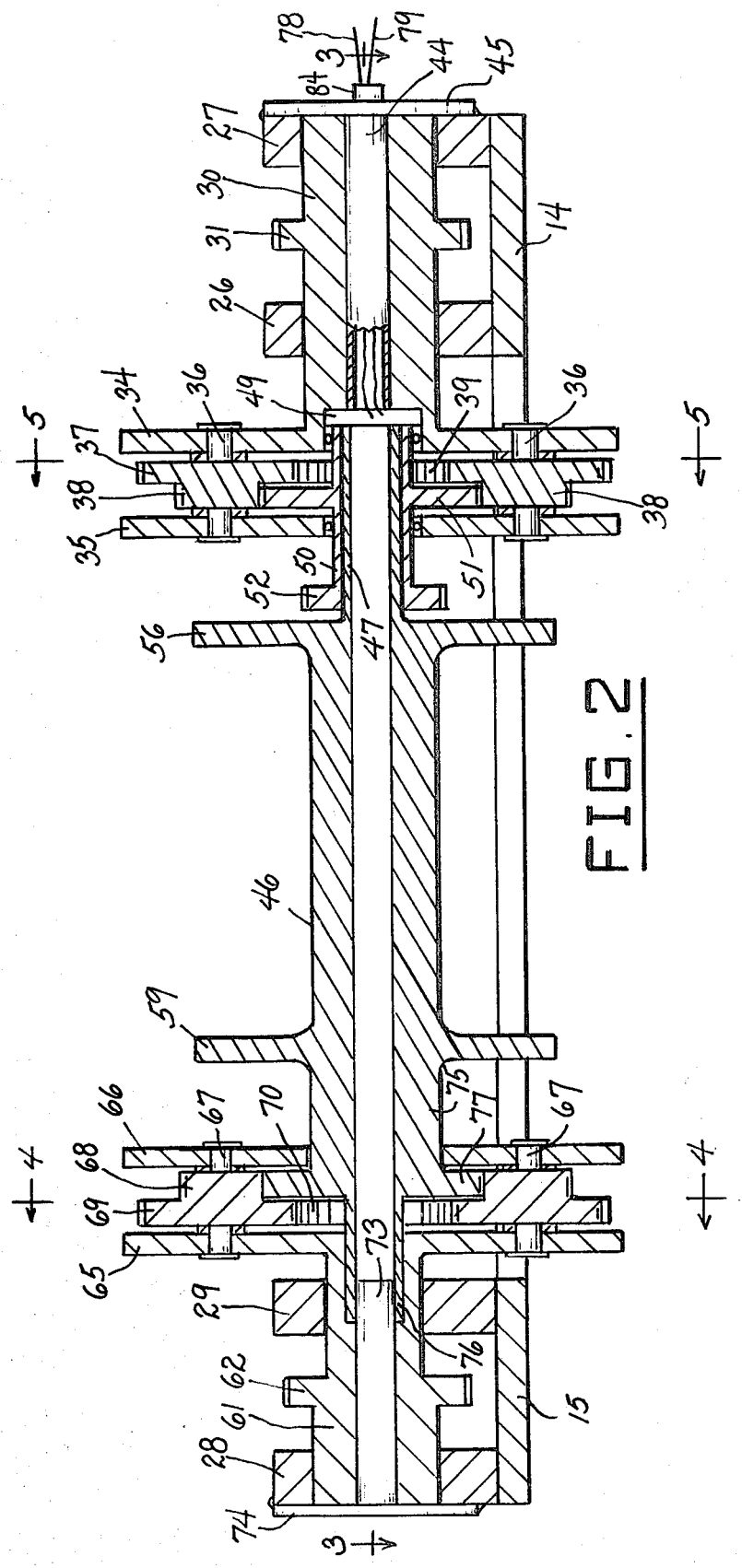
FIG. 2 is an enlarged longitudinal vertical cross-sectional view taken through the apparatus substantially on the line 2—2 of FIG. 1.
Figure 3:
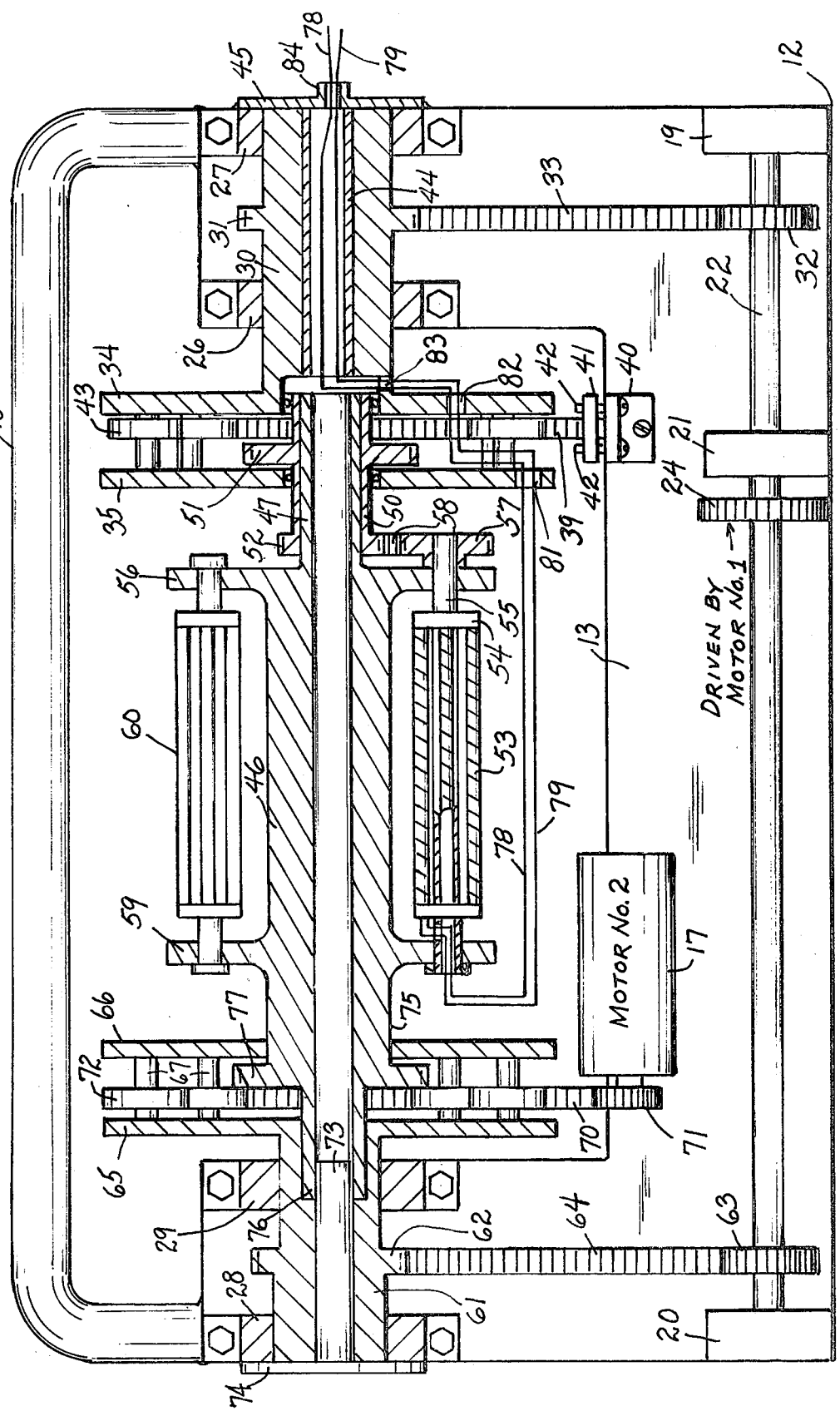
FIG. 3 is a horizontal cross-sectional view taken substantially on line 3—3 of FIG. 2.
Figure 4:
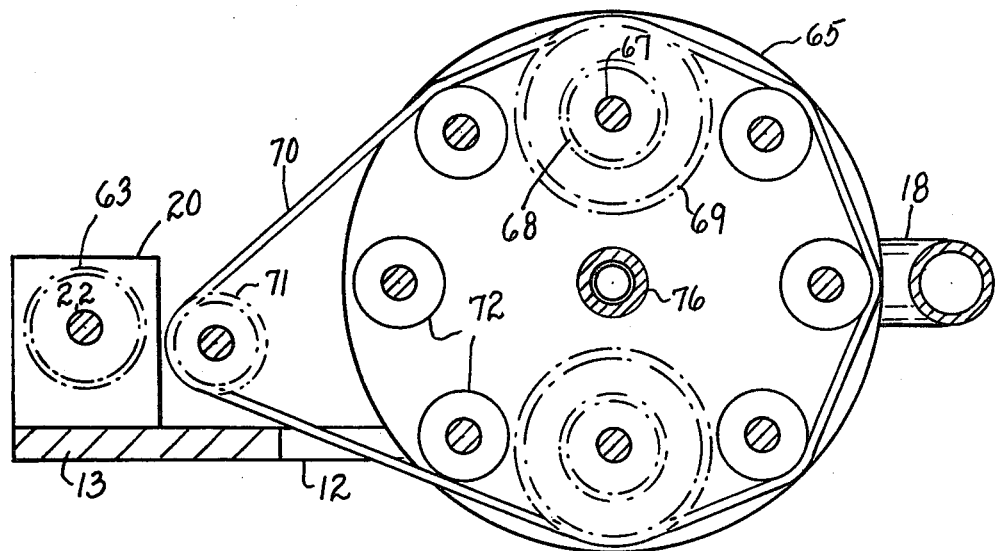
FIG. 4 is a transverse vertical cross-sectional view taken substantially on line 4—4 of FIG. 2.
Figure 5:
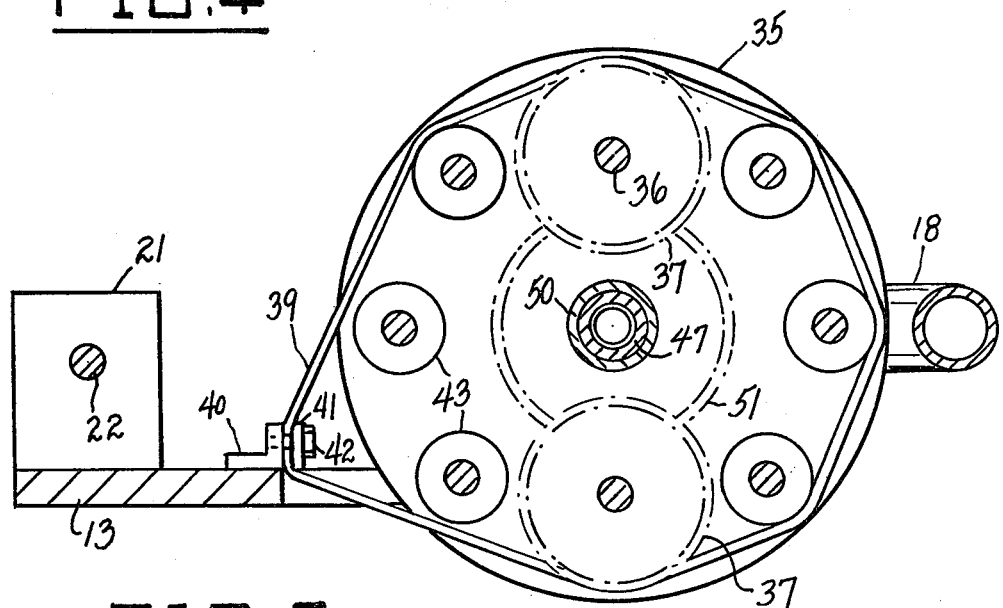
FIG. 5 is a transverse vertical cross-sectional view taken substantially on line 5—5 of FIG. 2.

Respectively secured on the end arm portions 14 and 15 (see FIG. 2) are longitudinally aligned pairs of pillow blocks 26, 27 and 28, 29. A hollow shaft 30 is journalled in the pillow blocks 26, 27 and has an integral gear 31 which is drivingly coupled to a gear 32 on shaft 22 via a toothed drive belt 33. Integrally formed with the inner end of hollow shaft 30 is a spider disc 34. A mating spider disc 35 is connected in spaced parallel coaxial relation to spider disc 34 by diametrically-opposed, end-flanged rotatable shafts 36, 36 on which are rigidly mounted stepped planetary gears 37, 38, the larger gears 37 being identical and being gearingly engageable with an endless toothed belt 39 fixedly secured to base plate 12 by being clamped between an angle bracket 40 secured on plate portion 13 and a clamping block 41 clampingly fastened to the upstanding arm of the bracket by clamping screws 42, 42 located on opposite sides of the belt, as shown in FIG. 3.

A plurality of spaced belt-supporting rollers 43 are journalled between the spider discs 34, 35, arranged between the stepped gears 37, 38 to present a substantially continuous circular belt-supporting array as the spider discs simultaneously rotate by the driving action of motor 16. Thus, the belt-supporting rollers 43 are located in the same transverse vertical plane as the planetary larger gears 37. Said idler rollers 43 act to keep the belt 39 in a roughly circular shape and enable the belt to act as an internal gear.

A stationary tubular shaft member 44 extends axially through the hollow shaft 30, the outer end thereof being rigidly secured to a centrally apertured disc member 45 which is in turn rigidly secured to pillow block 27. A column-supporting spool member 46 is provided at its right end, as viewed in FIGS. 2 and 3, with a hollow supporting shaft 47 which is rotatably surrounded by a sleeve member 50 which extends into and is journalled in an annular central recess 49 provided in hollow shaft 30. The sleeve member 50 rotatably surrounds shaft 47 and extends supportingly and rotatably through the center portion of spider member 35. Said sleeve member 50 is provided inwardly adjacent spider member 35 with a sun gear 51 which meshingly engages with the smaller planet gears 38, 38. At its leftward end the sleeve member 50 is provided with a gear 52.

A conventional coiled column 53 is mounted on a column holder 54 which has an axial hollow shaft 55. The right end portion of shaft 55 is rotatably supported in the right flange 56 of spool member 46 and has secured thereon a gear 57, identical to gear 52 and drivingly coupled thereto by a toothed belt 58. The left end portion of shaft 55 is journalled in the left flange 59 of spool member 46.

A suitable counterweight member 60 is mounted between the spool flanges 59, 56 diametrically opposite to and in counterbalancing relation with the column holder 54 and the column 53 carried thereby.

A hollow shaft 61 is journalled in the pillow blocks 28, 29 and has an integral gear 62, similar to the gear 31, which is drivingly coupled to a gear 63 on shaft 22 via a toothed drive belt 64. Integrally formed with the inner end of hollow shaft 61 is a spider disc 65. A mating spider disc 66 is connected in spaced parallel coaxial relation to spider disc 65 by diametrically-opposed end-flanged rotatable shafts 67, 67 on which are rigidly mounted stepped planetary gears 68, 69, the larger gears 69 being identical and being gearingly engageable with a toothed drive belt 70, which in turn is meshingly engaged with a driving gear 71 on the shaft of motor 17. A plurality of spaced belt-supporting rollers 72, similar to the previously described idler rollers 43, are journalled between the spider discs 65, 66, arranged between the stepped gears 68, 69 to present a substantially continuous circular belt-supporting array as the spider discs 65, 66 simultaneously rotate by the action of motor 16. Thus, the belt-supporting idlers 72 are located in the same transverse vertical plane as the planetary larger gears 69 and act to keep the belt 70 in a roughly circular shape and enable the belt to act as an internal gear.

A stationary shaft member 73 extends axially through the hollow shaft 61, the outer end thereof being rigidly secured to a disc member 74 which is in turn rigidly secured to pillow block 28. The spool member 46 has a shaft portion 75 which extends rotatably through spider member 66 and which has a reduced tubular end portion 76 extending rotatably through spider member 65 and being journalled on stationary shaft 73, as shown in FIGS. 2 and 3. The spool shaft portion 75 is provided at its end with an integral sun gear 77 which meshingly engages the smaller planet gears 68, 68.

The flow tubes, shown at 78 and 79, as viewed in FIG. 3, pass through an opening in hollow shaft 55 inwardly adjacent spool flange 59, thence through the left end portion of shaft 55, thence through openings 81 and 82 in spider members 35 and 34, thence through a passage 83 in the wall of hollow shaft 30, thence through the stationary tubular shaft 44, and thence out through a central conduit element 84 on disc member 45.

The column 53 is rotated on the spool 46 responsive to the rotation of the spider structure 34, 35 when motor 16 is energized, by a gearing system comprising the fixed belt 39, acting as an internal gear, the planetary gears 37 in mesh therewith, the smaller planetary gears 38 integral with the gears 37, the sun gear 51 driven by the gears 38, the gear 52 integral with sun gear 51, the drive belt 58, and gear 57 mounted on the shaft 55 of the column 53. Gears 52 and 57 are identical. The gear train is designed so that sun gear 51, and hence column shaft 55, is rotated at twice the rate of rotation of the spider structure 34, 35.

The spool 46 is driven by the second motor 17 via gear 71, belt 70 and planet gear elements 69, which may thereby provide an additional increment of revolutional speed $\Delta W$. As shown in FIG. 2, the smaller planet gears 68 mesh with the spool gear 77 to drive the spool.

In operation, motor 16 turns spider structures 34, 35 and 65, 66 via the gear-and-belt systems including drive belts 25, 33 and 64 at a rotational velocity $W_1$. Thus, the sun gear 51 and the attached sleeve 50 rotate at a rotational velocity $2 \cdot W_1$. The coil drive belt 58 then assures that the coiled columns 53 will also rotate at $2 \cdot W_1$ about the column axis with respect to the laboratory frame support 12, regardless of their orbital velocity produced by the revolution of the support spool 64. The fluid flow tubes 78, 79 therefore do not become twisted or tangled. The second motor 17 causes the sun gear 77 and the support spool 46 to rotate at $(2 \cdot W_1) + \Delta W$ and hence causes a centrifugal force field to be applied to the coiled column elements.

The idlers 72 and 43 keep the belts 39 and 70 in a roughly circular shape and enable said belts to act as internal gears without the expense, complications, and precision support structure necessary for true internal gears.

The centrifugal field holds the heavy phase in the loops of the coiled tubes, while the rotation of the coiled tubes with respect to the centrifugal field permits "Archimedes Screw" advance of the heavy phase when desired.

While a specific embodiment of an improved flow-through coil planet centrifuge device has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A flow-through coil planet centrifuge comprising a support, bearing means on the support defining a main rotational axis, two spaced spider structures journalled on said bearing means, spool means rotatably mounted between said spider structures for rotation on said axis, coiled centrifuge column means rotatably mounted on said spool means for rotation on a column axis spaced from and parallel to said main axis, a first independent stationary motor, means drivingly coupling said first motor to said two spider structures for simultaneous rotation thereof, fixed guide means on the support, inlet and outlet fluid conduit means connected to and in fluid communication with said column means and extending through said fixed guide means, column-rotating gearing means drivingly coupling a first one of said spider structures to said column means to rotate said column means responsive to rotation of said first spider structure, a second independent stationary motor, spool-rotating gearing means on the other spider structure, and means drivingly coupling said second motor to said spool-rotating gearing means to drive the spool means independently of the first motor.

2. The coil planet centrifuge of claim 1, and wherein said fixed guide means is tubular and is located on said main axis.

3. The coil planet centrifuge of claim 2, and wherein said tubular guide means is located outwardly adjacent to said first spider structure.

4. The coil planet centrifuge of claim 1, and wherein the column-rotating gearing means comprises fixed internal gear means surrounding the first spider structure, and coupling gear means between the first spider structure and the column means including a rotatable gear element on the first spider structure which is in meshing engagement with said fixed internal gear means.

5. The coil planet centrifuge of claim 4, and wherein said fixed internal gear means comprises a toothed belt fixedly secured to said support and extending around said first spider structure.

6. The coil planet centrifuge of claim 5, and wherein said first spider structure comprises a pair of spaced coaxial disc members with a plurality of rollers journalled therebetween and spaced to define a substantially circular support for said toothed belt.

7. The coil planet centrifuge of claim 5, and wherein said first spider structure comprises a pair of spaced coaxial disc members, said coupling gear means comprising a plurality of spaced planet gears journalled between the disc members and meshing with the toothed belt, said planet gears having auxiliary coaxial gears, sun gear means journalled axially in the first spider structure and meshing with said auxiliary gears, and means drivingly coupling said sun gear means to said column means.

8. The coil planet centrifuge of claim 7, and a plurality of rollers journalled between the disc members and located to define a substantially circular support for the toothed belt.

9. The coil planet centrifuge of claim 1, and wherein said spool-rotating gearing means comprises planet gearing on said other spider structure, and means gearingly coupling said planet gearing to said spool means, and wherein said means drivingly coupling said second motor to the spool-rotating gearing means comprises a toothed belt extending around said other spider structure and meshing with said planet gearing, said second motor having a drive gear meshingly engaged with said toothed belt.

10. The coil planet centrifuge of claim 9, and wherein said second spider structure comprises a pair of spaced coaxial disc members with a plurality of rollers journalled therebetween and spaced to define a substantially circular support for said toothed belt.

11. The coil planet centrifuge of claim 9, and wherein the column-rotating gearing means comprises fixed internal gear means surrounding the first spider structure, and coupling gear means between the first spider structure and the column means including at least one rotatable gear element on the first spider structure which is in meshing engagement with said fixed internal gear means.

12. The coil planet centrifuge of claim 11, and wherein said fixed internal gear means comprises another toothed belt fixedly secured to said support and extending around said first spider structure.

* * * * *